United States Patent [19]

Spence

[11] Patent Number: 5,733,304
[45] Date of Patent: Mar. 31, 1998

[54] DISPOSABLE INFLATABLE TOURNIQUET CUFF

[75] Inventor: Jerry L. Spence, Snohomish, Wash.

[73] Assignee: InstruMed, Inc., Bothell, Wash.

[21] Appl. No.: 701,100

[22] Filed: Aug. 21, 1996

[51] Int. Cl.⁶ .................................................. A61B 17/00
[52] U.S. Cl. ................................................ 606/203; 128/686
[58] Field of Search ............................. 606/202, 203, 606/204; D24/143; 128/686, DIG. 20, DIG. 15; 383/3

[56] References Cited

U.S. PATENT DOCUMENTS

| | | |
|---|---|---|
| 800,467 | 9/1905 | Myers . |
| 814,795 | 3/1906 | Myers . |
| 2,347,197 | 4/1944 | Liberte ........................ 128/327 |
| 2,511,269 | 6/1950 | Jones .......................... 128/327 |
| 3,120,846 | 2/1964 | Fletcher ...................... 128/327 |
| 3,467,077 | 9/1969 | Cohen ........................ 128/2.05 |
| 3,504,675 | 4/1970 | Bishop, Jr. ................. 128/327 |
| 3,633,567 | 1/1972 | Sarnoff ...................... 128/2.05 |
| 3,654,931 | 4/1972 | Hazlewood ................. 128/327 |
| 3,669,096 | 6/1972 | Hurwitz ..................... 128/2.05 |
| 3,670,735 | 6/1972 | Hazlewood ................. 128/327 |
| 3,713,446 | 1/1973 | Sarnoff ...................... 128/327 |
| 3,756,239 | 9/1973 | Smythe ...................... 128/327 |
| 3,906,937 | 9/1975 | Aronson .................... 128/2.05 |
| 3,930,506 | 1/1976 | Overend .................... 128/327 |
| 3,946,731 | 3/1976 | Lichtenstein ............... 128/214 |
| 3,968,788 | 7/1976 | Hopkins .................... 128/2.05 |
| 3,977,393 | 8/1976 | Kovacic .................... 128/2.05 |
| 3,985,123 | 10/1976 | Herzlinger et al. ......... 128/2.05 |
| 4,106,499 | 8/1978 | Ueda ......................... 128/2.05 |
| 4,149,540 | 4/1979 | Hasslinger ................. 128/327 |
| 4,177,813 | 12/1979 | Miller et al. ............... 128/326 |
| 4,321,929 | 3/1982 | Lemelson et al. .......... 128/630 |
| 4,326,513 | 4/1982 | Schulz et al. ............ 128/203.14 |
| 4,353,374 | 10/1982 | Rebbe et al. ............... 128/686 |
| 4,354,503 | 10/1982 | Golden ...................... 128/686 |
| 4,406,281 | 9/1983 | Hubbard et al. ............ 128/132 |
| 4,465,076 | 8/1984 | Sturgeon ................... 128/686 |
| 4,635,635 | 1/1987 | Robinette-Lehman ...... 128/327 |
| 4,727,885 | 3/1988 | Ruff .......................... 128/686 |
| 4,920,971 | 5/1990 | Blessinger ................. 128/679 |

(List continued on next page.)

FOREIGN PATENT DOCUMENTS 515785  4/1921  France .................. 606/203

OTHER PUBLICATIONS

DePuy Inc.'s one page advertisement for disposable tourniquet cuffs. 1992.

Primary Examiner—Michael Buiz
Assistant Examiner—Nancy Connoly Mulcare
Attorney, Agent, or Firm—Gregory W. Moravan

[57] ABSTRACT

A disposable inflatable tourniquet cuff which may include an inflatable bladder having inner and outer walls which, in order to reduce cost and complexity, may be of the same size and made from the same material. A stiffener may be located within the bladder's inflatable fluid space, to eliminate the need for any separate parts to properly locate or hold the stiffener. The walls may have exterior, velcro-type soft, fuzzy loops or filaments; and be secured together with welds having a width selected to prevent the longitudinal sides of the cuff from spontaneously rolling up. The soft, fuzzy inner wall may serve as the patient contacting part of the cuff, thereby eliminating the need for a separate soft, fuzzy inner cover to protect the patient; and may serve to engage the hook-type velcro surface on other parts of the cuff, to hold them in the desired position. The soft, fuzzy outer wall may serve to engage the hook-type velcro on certain other parts of the cuff; as well as to engage the hook-type velcro on both the anchored and free surfaces of the strap that is used to hold the cuff in place on the patient's limb. An anchoring and alignment patch or tab may be provided to assist in the anchoring and even winding of the cuff about the patient's limb. During use of the tourniquet cuff, the strap may also serve as a stiffener to limit the outward movement of the bladder's outer wall when the bladder is inflated, thereby eliminating the need for a separate stiffener element to serve this function.

16 Claims, 2 Drawing Sheets

U.S. PATENT DOCUMENTS

| | | | |
|---|---|---|---|
| 4,979,953 | 12/1990 | Spence | 606/202 |
| 5,193,549 | 3/1993 | Bellin et al. | 128/686 |
| 5,201,758 | 4/1993 | Glover | 606/202 |
| 5,312,431 | 5/1994 | McEwen | 606/202 |
| 5,396,894 | 3/1995 | Eide et al. | 128/686 |
| 5,411,518 | 5/1995 | Goldstein et al. | |

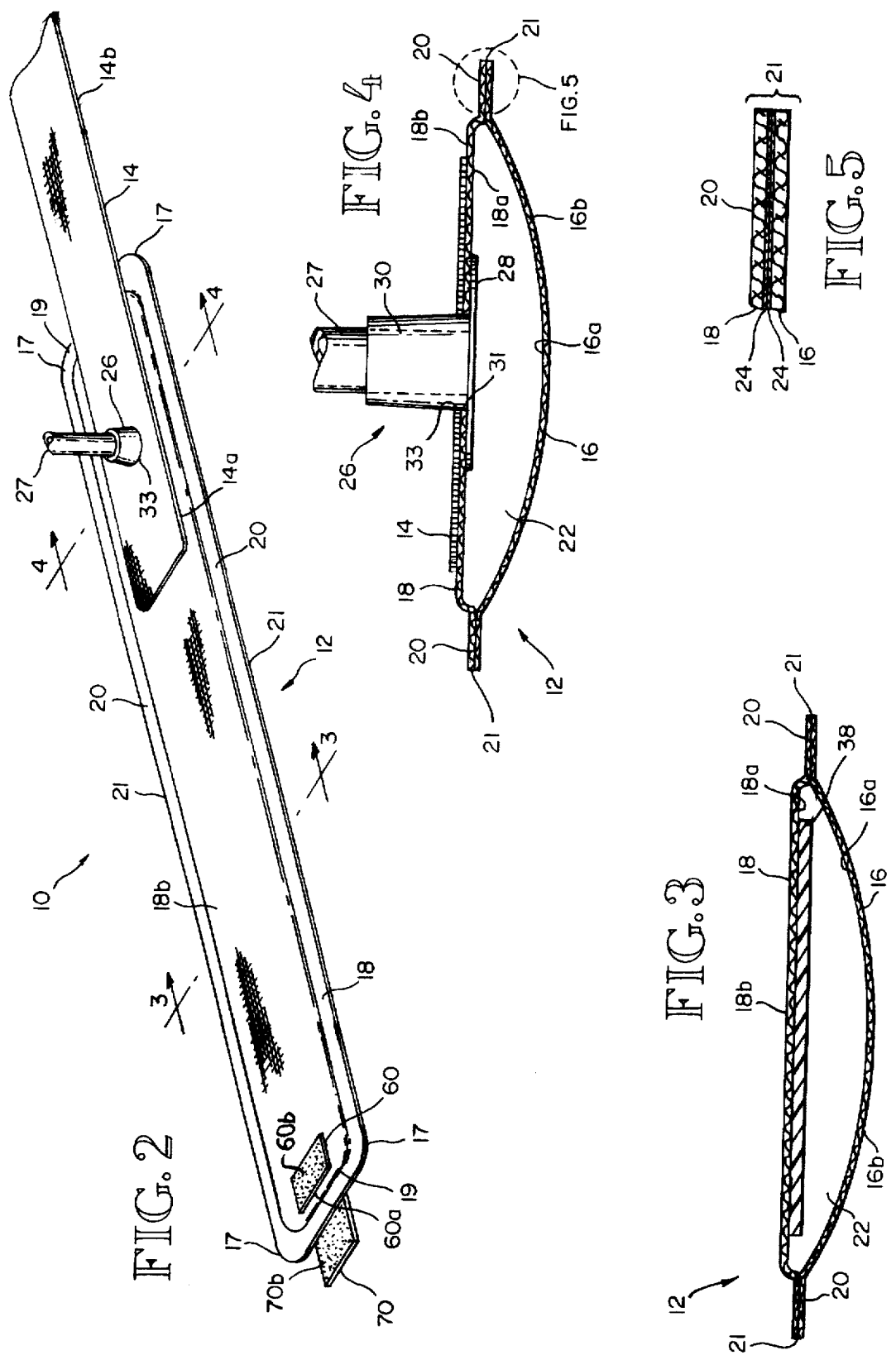

DISPOSABLE INFLATABLE TOURNIQUET CUFF

BACKGROUND OF THE INVENTION

The present invention relates to tourniquets. More particularly, it relates to disposable inflatable tourniquet cuffs of the type that are wrapped around a limb of the patient, and which are then inflated to provide pressure for controlling, or even stopping, the flow of fluids, such as blood, lymph or medication, through that limb.

SUMMARY OF THE INVENTION

The term patient is used herein to include both human and animal patients, since the present invention may be used on both.

During many surgical procedures, the tourniquet cuff of the present invention may used to completely stop the flow of fluids, such as blood, through a limb of the patient. For example, such stopping of fluid flow may be necessary during the amputation of all or part of the limb, in order to prevent the death of the patient from the loss of blood.

During less drastic surgical procedures, such as during a surgical repair of the patient's hand, for example, the tourniquet cuff of the present invention may be used for controlling the flow of fluids, such as blood and medication, through the affected limb, rather than for completely stopping them. Such control of fluid flow through the affected limb may be used to help achieve at least two important goals.

The first important goal may be that tourniquet cuff may help to force any locally injected anesthetic to dwell longer near the sites where it was originally injected, until the anesthetic has had a chance to become effective, rather than being immediately carried away by the patient's blood stream. This may be desirable because less of the locally injected anesthetic may then be needed to obtain the desired degree of anesthesia of the surgical site, than may otherwise be the case.

Controlling the spread of the locally injected anesthetic away from the sites where it was originally injected may also be desirable since it may greatly reduce, if not effectively eliminate, the amount of the injected anesthetic that reaches other portions of the patient's body, where it is not needed, and where it may have harmful side effects.

In other words, it is, in general, always desirable to use the minimum medically effective dose of any anesthetic or other medication, and to restrict the spread of that anesthetic or other medication beyond the portions of the patient's body where it is needed.

The second important goal that may be achieved by using the tourniquet cuff of the present invention for controlling the flow of fluids through the patient's limb is to reduce, or effectively prevent, the harmful or even fatal, loss of vital bodily fluids such as blood from the affected limb during the surgery itself.

In order to prevent infection and cross-infection between patients, tourniquet cuffs must either be cleaned and sterilized between uses; or they must be disposable. Thus, before a disposable tourniquet cuff can be a commercially successful product, it's cost to the end user must be less than the cost of cleaning and sterilizing a conventional, non-disposable tourniquet cuff.

However, it is not easy to make a commercially successful disposable tourniquet cuff, since the twin goals of reliability and low cost may tend to be mutually exclusive. That is, the reliability of any tourniquet cuff may tend to decrease as its cost decreases; while the cost of any tourniquet cuff may tend to increase as its reliability increases. However, the disposable tourniquet cuff of the present invention simultaneously attains the twin goals of reliability and low cost, while still permitting its manufacturers and distributors to make a reasonable profit.

In order to make a disposable tourniquet cuff which is both reliable and low in cost, it is important to minimize number of parts from which the tourniquet cuff is made; and to minimize the cost of assembling those parts into the completed tourniquet cuff. The tourniquet cuff of the present invention may help to achieve both of those important goals.

The tourniquet cuff of the present invention may attain the goal of minimizing the number of its different parts by, for example, (a) eliminating certain separate parts previously thought to be required for certain conventional disposable tourniquet cuffs; (b) by having certain of its parts perform multiple functions, instead of having each of those functions being performed by the separate parts of certain conventional disposable tourniquet cuffs; and/or (c) by making certain of its parts identical.

The tourniquet cuff of the present invention may attain the goal of minimizing the cost of assembling its parts into a completed tourniquet cuff by using one or more of at least the following three techniques: (a) by simultaneously securing together certain of its parts during one manufacturing step; (b) by eliminating the need to use costly, slow, and leak prone sewing or stitching to secure any of its parts together; and/or (c) by using low cost, fast and reliable welding to secure certain of its parts together.

In one form, the tourniquet cuff of the present invention may comprise an inflatable bladder, a stiffener located within the bladder, and a strap for securing the inflatable bladder in the desired location about the patient's limb.

By locating the stiffener within the bladder, the need for a separate means for holding the bladder in position in the tourniquet cuff may be eliminated, thereby simplifying and reducing the cost of the present invention.

During use of the present invention, the bladder is first wound evenly around the patient's limb, and then secured in place with the strap. The bladder is then inflated to the desired degree, so that the pressure exerted by the tourniquet cuff on the patient's limb reduces, or even stops, the flow of fluids through the patient's limb.

The bladder may have a fixed end, which is end of the bladder that is in contact with the patient's limb during use of the tourniquet cuff. The fixed end of the bladder may be provided with an anchoring and aligning tab or patch. Such a tab or patch may serve at least two important functions. First, they may help to anchor an overlapping, free portion of the bladder with respect to the bladder's fixed end, in order to help hold the tourniquet cuff in place on the patient's limb while the tourniquet cuff is being applied to the patient's limb.

The second important function that the anchoring and aligning tab or patch may serve is to help to align an overlapping, free portion of the bladder with respect to the bladder's fixed end, in order to help the cuff's overlapping, free portion to be wound evenly over the bladder's fixed end, rather than being wound in an undesirable spiral. This may be important since otherwise valuable, sometimes critical, time may have to be taken to repeatedly re-apply the tourniquet cuff to the patient's limb, until it is wound evenly around the patient's limb. Such even winding of the tourniquet cuff about the patient's limb may be important since otherwise the tourniquet cuff may not be able to exert the desired, uniform pressure on the patient limb.

The anchoring and aligning tab may comprise a strip of velcro-compatible material having an anchored inner surface permanently velcroed to the inner wall of the fixed end of the bladder; thereby eliminating the need for using costly and time-consuming sewing or stitching for this purpose, which might also cause the bladder to tend to leak. The tab may also have a free inner surface adapted to be releasably velcroed to an overlapping portion of the bladder's inner wall when the tourniquet cuff is being wound about the patient's limb.

Alternatively, the anchoring and aligning patch may comprise a velcro patch having an inner surface permanently velcroed to the outer wall of the fixed end of the bladder; thereby eliminating the need for using costly and time-consuming sewing or stitching for this purpose, which might also cause the bladder to tend to leak. The outer surface of the velcro patch may be adapted to be releasably velcroed to an overlapping portion of the inner wall of the bladder when the tourniquet cuff is being wound about the patient's limb.

When the tourniquet cuff is inflated during use, the stiffener may be forced against the inside of the bladder's outer wall by the fluid used to inflate the bladder. This may help the tourniquet cuff to exert a more uniform pressure on the patient's limb.

The bladder may be generally rectangular in shape, and its four corners may be radiused. Sharp, 90° corners on the bladder may not be desirable, since they may tend to dig into the patient's limb during use of the tourniquet cuff, and cause patient discomfort, or even injury.

The inflatable bladder may comprise an inner wall (that may contact the patient during use of the tourniquet cuff), and an outer wall (that may not contact the patient during use of the tourniquet cuff). The bladder's inner and outer walls may be secured together with end welds and longitudinal side welds; thereby eliminating the need for using costly and time-consuming sewing or stitching for this purpose, which might also cause the bladder to tend to leak. The bladder's inner and outer walls may be of the same size.

The bladder's longitudinal side welds may be at least about ¼ of an inch in width in order to make the longitudinal side welds stiff enough to at least partially prevent the longitudinal sides of the bladder from curling up towards the longitudinal centerline of the bladder. The stiffener may also serve the function of helping to prevent the longitudinal sides of the tourniquet cuff from curling up towards the longitudinal centerline of the bladder. Preventing such curling up of the bladder's longitudinal sides may help to prevent the tourniquet cuff from slipping on the patient's limb, while the tourniquet cuff is being applied to the patient's limb; and may help the tourniquet cuff to apply more uniform pressure to the patient's limb during use.

The bladder's inner wall may comprise a material having an fluid-tight inner surface, and an outer surface comprising velcro-type soft, fuzzy loops or filaments. The soft, fuzzy outer surface may help to prevent the tourniquet cuff from slipping when being applied to the patient's limb; may help protect the patient's skin from injury; may help to provide for increased patient comfort; and may act as a velcro-compatible surface for at least one other part of the tourniquet cuff, such as the anchoring and aligning tab or patch, for example. Since the bladder's inner wall may function as the inner wall of the tourniquet cuff itself, the need for a separate cover for the bladder's inner wall may be eliminated, thereby helping to reduce the complexity, number of parts, and cost of the tourniquet cuff.

The bladder's outer wall may also preferably comprise a material having an fluid-tight inner surface; and an outer surface comprising velcro-type soft, fuzzy loops or filaments. Thus, the bladder's inner and outer walls may share the commonalities of being of the same size, and being made from the same material. Such commonalities may help to simplify the tourniquet cuff, by reducing the number of different parts needed for it, thereby helping to reduce the complexity and cost of the tourniquet cuff.

Since the bladder's outer wall may also function as the outer wall of the tourniquet cuff itself, any need for a separate outer cover for the bladder may be eliminated, thereby further reducing the number of parts, complexity and cost of the tourniquet cuff.

The strap may comprise an anchored inner surface, which may be permanently velcroed to a corresponding portion of the bladder's outer wall; thereby eliminating the need for using costly and time-consuming sewing or stitching for this purpose, which might also cause the bladder to tend to leak.

The strap may also comprise a free inner surface, which may be adapted to be releasably velcroed to a corresponding portion of the bladder's outer wall, after the tourniquet cuff has been evenly wound about the patient's limb, in order to hold the tourniquet cuff securely in place around the patient's limb.

During use of tourniquet cuff, the strap and/or the stiffener, may act as means for preventing any substantial outward deflection of the bladder's outer wall away from the patient's body when the bladder is inflated. As a consequence, most, if not substantially all, of the expansion of the bladder will occur at its inner wall, towards the patient's limb, where it is needed; thereby helping the tourniquet cuff to exert a more uniform pressure on the patient's limb.

In a further aspect of the tourniquet cuff of the present invention the stiffener may be eliminated. In such a case, any undesired curling up of the longitudinal edges of the tourniquet cuff may be at least partially prevented by such means as, for example: (a) suitably selecting the width of the strap to be at least about equal to the width of the bladder; (b) suitably selecting the width of the bladder's longitudinal edge welds; and/or by (c) suitably selecting the stiffness of the materials from which the bladder's inner and outer walls may be made.

If the stiffener is eliminated, the strap may be sized at least about equal in width to the width of the inflatable fluid space within the bladder, in order to help restrain the bladder's outer wall from moving away from the patient's limb when the bladder is inflated during use of the tourniquet cuff. This will, in turn, cause most, if not all, of the expansion of the bladder to occur at the bladder's inner wall, where it is needed, and will help the tourniquet cuff to exert a more uniform pressure on the patient's limb.

It should be understood that the foregoing summary of the disposable inflatable tourniquet cuff of the present invention does not set forth all of its features, advantages, characteristics, structures, methods and/or processes; since these and further features, advantages, characteristics, structures, methods and/or processes of the present invention will be directly or inherently disclosed to those skilled in the art to which it pertains by all of the disclosures herein.

BRIEF DESCRIPTION OF THE FIGURES

FIG. 2 is an assembled perspective view of the disposable inflatable tourniquet cuff of the present invention;

FIG. 3 is a transverse cross-sectional view thereof taken along line 3—3 of FIG. 2;

FIG. 4 is a transverse cross-sectional view thereof taken along line 4—4 of FIG. 2; and FIG. 5 is an enlarged, transverse cross-sectional view of a portion(shown encircled in FIG. 4) of one of the longitudinal side welds of the disposable inflatable tourniquet cuff of the present invention.

DESCRIPTION OF THE PREFERRED EMBODIMENTS

Figure 1:
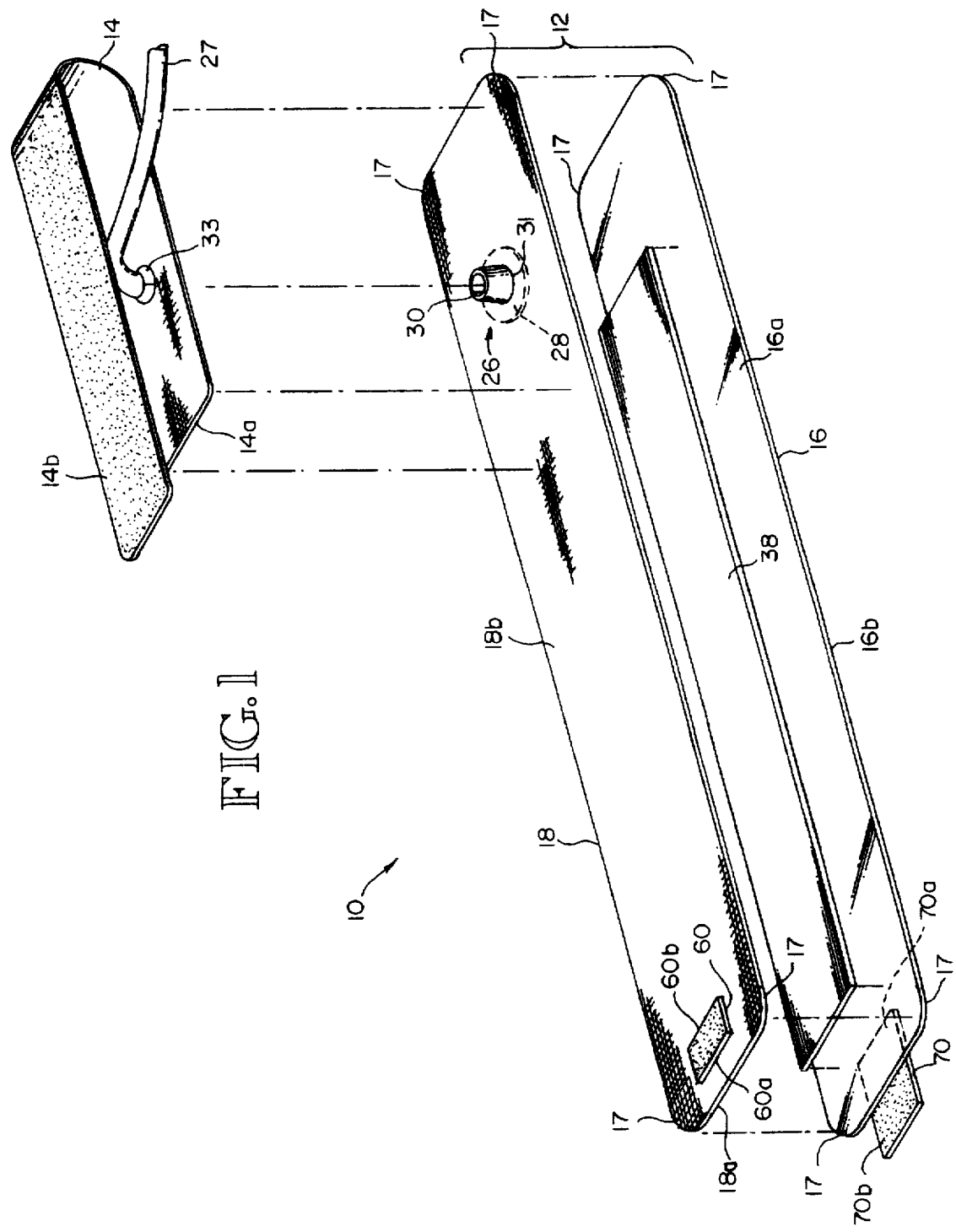
FIG. 1 is an exploded, perspective view of the disposable inflatable tourniquet cuff of the present invention.

Referring now to FIGS. 1–5, for patient safety the disposable inflatable tourniquet cuff 10 of the present invention may be made from non-toxic materials. The tourniquet cuff 10 may comprise an inflatable bladder 12; a stiffener 38 located within the bladder 12; a strap 14 for securing the bladder 12 to the patient's limb during use of the tourniquet cuff 10; and an anchoring and aligning means comprising an anchoring and aligning patch 60, or an anchoring and aligning tab 70.

Although both a patch 60 and a tab 70 are illustrated, the tourniquet cuff 10 may be provided with only one, or the other, since both the patch 60 and the tab 70 may serve similar functions. The patch 60 may have inner and outer surfaces 60a, 60b, respectively; and the tab 70 may have an anchored inner surface 70a and a free inner surface 70b.

The bladder 12 may comprise an inner wall 16, having inner and outer surfaces 16a, 16b; and an outer wall 18, having inner and outer surfaces 18a, 18b. As seen in FIGS. 1–2, it may be preferred that the corners 17 of the inner and outer walls 16, 18 not be sharp corners, but instead be radiused, to help prevent them from digging into the patient's limb during use of the tourniquet cuff 10. The ratio of the width of the bladder 12 to the radius of its corners 17 may on the order of about 2:1 to about 8:1, and preferably about 4:1. For example, if the bladder 12 had a width of about 3 inches, the corners may have about a ¾ inch radius.

The inner surfaces 16a, 18a may be sealed together with a pair of end welds 19 and a pair of longitudinal side welds 20, to form an inflatable fluid space 22 within the bladder 12.

As used herein, the terms "weld", "welding", "welded", and the like, encompass the use of radio frequency welding, heat welding, and/or adhesives, unless the context should indicate otherwise.

The use of welds 19, 20 to secure the peripheries of the walls 16, 18 together may be preferred since such welds may be quicker, easier, lower in cost, and more reliable. In contrast, using conventional sewing or stitching to secure the peripheries the walls 16, 18 together may be slower, more difficult, higher in cost, and may cause the bladder 12 to tend to leak.

The peripheral portions of the walls 16, 18 may be made from a substance which is compatible with the particular welding process which has been chosen to produce the welds 19, 20. Alternatively, the peripheral portions of the inner surfaces 16a, 18a may be impregnated, coated, or lined with a substance which is compatible with the particular welding process which has been chosen to produce the welds 19, 20. For example, if a radio frequency welding process is chosen, then said substance may be any suitable polymer, such as polyurethane.

The width of the welds 19, 20, and the welding process used to produce them, may be selected to have a strength sufficient to safely withstand, without leaking or rupturing, the maximum designed operating pressure within the inflatable fluid space 22.

The width of the longitudinal side welds 20 may be selected to make those welds stiff enough to at least partially prevent the bladder 12's longitudinal sides 21 from curling up towards the longitudinal centerline of the bladder 12 while the tourniquet cuff 10 is being secured to the patient's limb. The ratio of the overall width the bladder 12 to the width of each of its welds 20 may be on the order of from about 18:1 to about 6:1, and preferably about 12:1, in order to provide the welds 20 with the desired stiffness.

By way of example, if the bladder 12 had an overall width of about 3 inches, then each its welds 20 may be at least about ¼ of an inch in width.

Before the walls 16, 18 are welded together, a stiffener 38 may be located between them, within the inflatable fluid space 22; thereby eliminating the need for a separate cover or other element to hold the stiffener 38 in place on, or within, the tourniquet cuff 10.

By way of example, the stiffener 38 may comprise a sheet of polyvinylchloride (PVC) about 0.020 of an inch thick. As best seen in FIGS. 1–2, the stiffener 38's length may be selected to be about equal to the distance between the left end weld 19 and the flange 28 on the inlet/outlet fitting 26.

By selecting the stiffener 38's width to be about equal to the distance between the side welds 20, the stiffener 38 may help to prevent the bladder 12's longitudinal sides 21 from curling up towards the bladder 12's longitudinal centerline while the tourniquet cuff 10 is being evenly wound about the patient's limb. This may enable the tourniquet cuff 10 to be more easily and quickly applied in a proper fashion to the patient's limb.

By selecting the stiffener 38's width be slightly less than the distance between the side welds 20, and/or by providing the stiffener with one or more perforations, the inflation fluid for the inflatable fluid space 22 may be permitted to more easily move between the stiffener 38 and the inner wall 16 when the tourniquet cuff 10 is inflated. As a result, when the tourniquet cuff 10 is inflated the inflation fluid may more easily force the stiffener 38 against the outer wall 18, so that the stiffener 38 may: (a) help to limit the outward deflection of the outer wall 18 when the fluid space 22 is inflated, thereby permitting most, of not all, of the expansion of the bladder 12 to occur at its inner wall 16, where it is needed to compress the patient's limb; and (b) may help enable the inner wall 16 to exert a more uniform pressure on the patient's limb.

Alternatively, the stiffener 38 may be eliminated. In such an event the strap 14 may be selected to have a width, strength and/or stiffness sufficient so that the strap 14 may perform one or more of the function(s) of the stiffener 38. In particular, the width of the strap 14 may be selected to be at least about equal to the distance between the side welds 20.

The bladder 12 may be provided with an inlet/outlet fitting 26 for permitting fluid to enter its fluid space 22 from an inlet/outlet tube 27, when the fluid space 22 is inflated; and for permitting fluid to exit from its fluid space 22 through the inlet/outlet tube 27, when the fluid space 22 is deflated.

The fluid space 22 may be inflated with any non-toxic fluid, whether that fluid be a gas (such as air) or a liquid (such as water), as long as that fluid is also compatible with the materials from which the tourniquet cuff is made.

The fitting 26 may be made of any suitable material, and may be of any suitable construction. For example, the fitting 26 may be made from polyurethane and may comprise a circular flange 28, and a hollow neck 30 which extends outwardly through corresponding holes 31, 33 in the outer wall 18 and the strap 14, respectively.

The circular flange 28 may be welded to the wall 18's inner surface 18a. Preferably, such welding may be done prior to the formation of the bladder's welds 19, 20.

The inlet/outlet tube 27 may be made from any suitable material, such as polyurethane. The tube 27 and the fitting 26's neck 30 may be permanently sealed together with an fluid-tight fit in any suitable way, such as by welding. Although one end of the tube 27 is illustrated as being located inside of the neck 30, it may be located around the outside of the neck 30. The free end of the tube 27 may be adapted to be connected to any suitable fluid input/output/control means for the fluid space 22.

Turning now to the anchoring and aligning patch 60, its inner surface 60a may be permanently secured to a corresponding portion of the outer surface 18b of the wall 18 by the use of a velcro-type connection between the surfaces 18b, 60a. For such a connection, the surface 18b may comprise velcro-type soft, fuzzy loops or filaments, and the surface 60a may comprise complimentary, velcro-type hooks; or vice versa. Alternatively, although it may be more time consuming and costly, the surfaces 18b, 60a may be welded together. In either event, the need for using costly and time-consuming sewing or stitching to permanently secure the surfaces 18b, 60a together, which might also cause the bladder 12 to tend to leak, may be eliminated.

The patch 60's outer surface 60b may comprise velcro-type hooks, and the outer surface 16b of the wall 16 may comprise complimentary, velcro-type soft, fuzzy loops or filaments; or vice versa. This may enable the surface 60b to be releasably secured to a corresponding portion of the surface 16b, as the bladder 12 is being evenly wound about the patient's limb.

Turning now to the anchoring and aligning tab 70, its anchored inner surface 70a may be permanently secured to a corresponding portion of the outer surface 16b of the wall 16 by the use of a velcro-type connection between the surfaces 16b, 70a. For such a connection, the surface 16b may comprise velcro-type soft, fuzzy loops or filaments, and the surface 70a may comprise complimentary, velcro-type hooks; or vice versa. Alternatively, although it may be more time consuming and costly, the surfaces 16b, 70a may be welded together. In either event, the need for using costly and time-consuming sewing or stitching to permanently secure the surfaces 16b, 70a together, which might also cause the bladder 12 to tend to leak, may be eliminated.

The tab 70's free inner surface 70b may comprise velcro-type hooks, and the outer surface 16b of the wall 16 may comprise complimentary, velcro-type soft, fuzzy loops or filaments; or vice versa. This may enable the surface 70b to be releasably secured a corresponding portion of the surface 16b as the bladder 12 is being evenly wound about the patient's limb.

The bladder 12's inner and outer walls 16, 18 may comprise any suitable strong, flexible material which is inherently fluid-tight, such as a sheet material made from plastic, rubber or polymer.

Alternatively, the walls 16, 18 may be made from any suitable strong, flexible porous material, such as a natural or synthetic fabric or cloth. In such a case, the walls 16, 18 may be made fluid-tight in any suitable way, such as by being impregnated, coated, or lined with a layer of fluid-tight material; or the walls 16, 18 may enclose an inflatable fluid-tight pouch or sack, within which the fluid space 22 may then be located.

The thickness of the walls 16, 18, and the material(s) from which they are made, may be selected so that they may have a strength which is sufficient to safely withstand, without leaking or rupturing, the maximum designed operating pressure within the inflatable fluid space 22.

The wall 16's outer surface 16b and/or the wall 18's outer surface 18b may comprise either velcro-type soft, fuzzy loops or filaments, or velcro-type hooks.

It may be preferred that the walls 16, 18 be of the same size, and/or that their respective outer surfaces 16b, 18b both comprise either velcro-type soft, fuzzy loops or filaments, or both comprise velcro-type hooks. Such commonality may offer the advantages of reducing the number of materials and/or the number of parts from which the tourniquet cuff 10 may be made, thereby simplifying its manufacture and reducing its cost.

Since the surface 16b is the patient contacting surface of the tourniquet cuff 10, it may be preferred that the surface 16b comprises velcro-type soft, fuzzy loops or filaments, in order to help to: (a) prevent the tourniquet cuff 10 from slipping while it is being wound about the patient's limb; (b) to reduce the possibility of injury to the patient; and/or (c) to increase the patient's comfort. Such a surface 16b may also offer the advantage of reducing the cost and number of parts required for the tourniquet cuff 10, by eliminating the need for the tourniquet cuff 10 to have a relatively costly, time consuming, and difficult to assemble separate inner cover to serve those purposes.

It is to be noted that if the surface 16b comprises velcro-type soft, fuzzy loops or filaments, then the tourniquet cuff 10 may offer the additional advantages of permitting: (a) the use of a releasable velcro-type connection between the surface 16b and the outer surface 60b of the anchoring and aligning patch 60; (b) the use of a permanent velcro-type connection between the surface 16b and the inner anchored surface 70a of the anchoring and aligning tab 70; and/or (c) the use of a releasable velcro-type connection between the surface 16b and the tab 70's free inner surface 70b.

If this is the case, then the surfaces 60b, 70a, 70b may comprise velcro-type hooks for engaging corresponding portions of the surface 16b's velcro-type soft, fuzzy loops or filaments. It will be recalled that such velcro-type connections may be preferred over welded, sewn or stitched connections because they may be less time consuming and less costly to manufacture, and less likely to cause the bladder 12 to tend to leak.

The strap 14 may comprise an anchored inner surface 14a and a free inner surface 14b. Preferably, the surface 14a may be permanently secured to the outer surface 18b of the wall 18, as best seen in FIG. 2, by the use of a velcro-type connection between the surfaces 14a, 18b. The neck 26 of the inlet/outlet fitting 24 may also help to permanently secure the surfaces 14a, 18b together, by helping to prevent any lateral movement of the surfaces 14a, 18b with respect to each other.

For a velcro-type connection between the surfaces 18b, 14a, the surface 18b may comprise velcro-type soft, fuzzy loops or filaments and the surface 14a may comprise complimentary, velcro-type hooks; or vice versa. Alternatively, although it may be more time consuming and costly, the surfaces 18b, 14a may be welded together. In either event, the need for using costly and time-consuming sewing or stitching to permanently secure the surfaces 18b, 14a together, which might also cause the bladder 12 to tend to leak, may be eliminated.

The strap 14's free inner surface 14b may be releasably secured to a corresponding portion of the surface 18b by the use of a velcro-type connection between the surfaces 14b, 18b; or by the use of hooks, snaps, buckles, ties, or other conventional releasable fastening means.

As was discussed above, it may be preferred that the wall 18's outer surface 18b comprises velcro-type soft, fuzzy loops or filaments. In such an event, the surfaces 14a, 14b of the strap 14, and the surface 60a of the anchoring and aligning tab 60, may comprise velcro-type hooks for engaging corresponding respective portions of the surface 18b's velcro-type soft, fuzzy loops or filaments. The length of the strap 14's free inner surface 14b may be selected to be, for example, equal to about half of the length of the bladder 12.

Turning again now to the inner and outer walls 16, 18, they may preferably be made, for example, from tricot.

As used herein, the term "tricot" is defined to mean any cloth, fabric, or other material having an outer surface which comprises velcro-type fuzzy loops or filaments that are suitable for engaging corresponding velcro-type hooks.

If the walls 16, 18 are made from tricot, then their outer surfaces 16b, 18b, will comprise velcro-type soft, fuzzy loops or filaments.

A suitable tricot may, for example, comprise a 200 heavy denier fabric or cloth weighing at least about three ounces per square yard.

If the particular tricot selected happens to be porous, its inner surface may be impregnated, coated or lined with a layer 24 of any suitable fluid-tight material, so that the inner surfaces 16a, 18a of the walls 16, 18 may also be fluid-tight. The fluid-tight material may be a polymer, such as polyurethane, and may be a coating about 0.003 inches thick. The layer 24 may also serve the purpose of helping the bladder 12's welds 19, 20 to be formed more easily and securely formed. Naturally, the layer 24 may not be needed if the particular tricot selected already comes with an inner, fluid-tight surface.

Referring now to FIGS. 1-2, the tourniquet cuff 10 may be installed by first placing the bladder 12's left, fixed end in the desired location on the patent's limb, with the surface 16b of its wall 16 in contact with the patient limb. The free portion of the bladder 12 may then wrapped about the patient's limb, with its surface 16b in contact with the patient's limb, until the surface 16b starts to overlap the surface 18b of the wall 18.

At that time, the outer surface 60 b of the anchoring and aligning patch 60 may then releasably engage the corresponding, overlapping portion of the surface 16b. The surfaces 60 b, 16b may be releasably engaged in a way such that the overlapping portion of the surface 16b may be anchored and aligned with respect to the bladder 12's fixed end. As a result, the remaining free portion of the bladder 12 may be wound evenly over the previously wound portions of the bladder 12, rather than being undesirably wound in a spiral around the patient's limb.

Such even winding of the bladder 12 over itself around the patient's limb may serve the important function of enabling the tourniquet cuff 10 to more properly, and accurately, exert the desired uniform pressure, in the desired location, on the patient's limb.

Alternatively, as has been mentioned, instead of using an anchoring and aligning patch 60, an anchoring and aligning tab 70 may be used. If the tab 70 is used, then during the installation of the tourniquet cuff 10, when the surface 16b first starts to overlap the surface 18b of the wall 18, the free inner surface 70b of the tab 70 may then releasably engage the corresponding, overlapping portion of the surface 16b. The surfaces 70b, 16b may be releasably engaged in such a way such that the overlapping portion of the surface 16b may be anchored and aligned with respect to the bladder's fixed end. As a result, the remaining free portion of the bladder 12 may be wound evenly over the previously wound portions of the bladder 12, rather than being undesirably wound in a spiral around the patient's limb.

After the bladder 12 has been fully, and evenly, wound about the patient's limb, the strap 14's free inner surface 14b may then be releasably secured to the outer surface 18b of the wall 18, to securely hold the tourniquet cuff 10 in the desired location on the patient limb.

Preferably, the bladder 12 may be sized long enough so that it will completely encircle the patient's limb at least once, with the bladder 12's ends overlapping each other.

Once the strap 14's surface 14b has been releasably secured to the surface 18b of the wall 18, the bladder 12's fluid space 22 may then be inflated through the inlet/outlet tube 27 and fitting 26 with any suitable fluid under pressure, such as air. As the bladder 12 is inflated more and more, its inner wall 16 presses against the patient's limb harder and harder, until the circulation of blood and other fluids through the patient's limb is retarded to the desired degree, or even completely stopped.

When the tourniquet cuff 10 is no longer needed, the fluid within the fluid space 22 may be released through the fitting 26 and inlet/outlet tube 27; the strap 14's surface 70b may be disengaged from the outer surface 18b of the wall 18; and the bladder 12 may be unwrapped from the patient's limb.

The tourniquet cuff 10 of the present invention may be sized for use on any size of limb. For example, a tourniquet cuff 10 which is suitable for use on an arm of an average human adult may have an overall width of about 3 inches, and an overall length (excluding the strap 14), of about 18 inches. Its strap 14 may be about 2½ inches wide and about 15½ inches long; and its stiffener 38 may be about 2¼ inches wide and about 14 inches long.

The tourniquet cuff 10 may include more than one inlet/outlet tube 27 and fitting 26 for inflating and deflating the fluid space 22. In such a case, addition holes 31, 33 may be provided in the wall 18 and strap 14, respectively, for the neck 30 of each additional fitting 26.

One problem associated with any tourniquet cuff, including the tourniquet cuff 10 of the present invention, is that if the patient is conscious during its use, and if the tourniquet cuff is used to severely constrict the patient's limb, then it may cause the patient great pain. The patent is, in fact, frequently conscious during an operation on one of his or her limbs, since surgeons often prefer to use a locally injected anesthetic in the vicinity of the surgical site, rather than a general anesthetic which renders the patient unconscious. This is because locally injected anesthetics generally expose the patient to fewer risks of adverse complications. Such locally injected anesthetics are more commonly known as "introduction of intravenous regional anesthesia" (IVRA).

To solve the pain problem caused by the tourniquet cuffs themselves on certain occasions, a conventional type of procedure, known as a Bier's block, may be used. A Bier's block may essentially comprise two tourniquet cuffs 10, located side by side, each of which may be independently inflated and deflated.

In order to better understand how a Bier's block works, let us assume that the Bier's block is to be used on a patient's upper arm, during an operation on the patient's lower arm in which a locally injected anesthetic is used.

Initially, only the Bier's block first tourniquet cuff, the one located closest to the patient's heart, is inflated. But it is only inflated to the relatively painless degree necessary to prevent any substantial flow of the locally injected anesthetic through the patient's limb past the inflated first tourniquet cuff. Thus, all of the patient's arm, up to the inflated first tourniquet cuff, will be quickly anesthetized.

When the desired degree of anesthesia has been obtained, the Bier's block second tourniquet cuff may then be inflated over an anesthetized portion of the patient's arm to whatever degree may be needed, which will cause the patient no discomfort at all. At that time the Bier's block first tourniquet cuff may then be deflated, since it is no longer needed.

In order to use the tourniquet cuff 10 of the present invention for a Bier's block, two separate tourniquet cuffs 10 may be used. Alternatively, the tourniquet cuff 10 may be provided with a bladder 12 and a strap 14 that are about twice as wide as the bladder 12 and the strap 14 that are illustrated in FIGS. 1–5. A dividing weld may then be provided longitudinally down the center of such a bladder 12, to form two separate bladders 12a, 12b, which are located side by side. Each bladder 12a, 12b would have its own respective an inflatable fluid space 22a, 22b.

Each bladder 12a, 12b may be provided with a separate stiffener 38, or one stiffener 38 may be used which may be about twice as wide as the stiffener 38 which is illustrated in FIGS. 1–5. A separate fitting 26a, 26b and a separate inlet/outlet 27a, 27b may be provided, respectively, for the bladders 12a, 12b. Similarly, for each fitting 26a, 26b, separate holes 31a, 31b and 33a, 33b may be provided, respectively, in the walls 18b of the bladders 12a, 12b and in the strap 14, of the tourniquet cuffs 10a, 10b. As was mentioned above, the strap 14 of the tourniquet cuffs 10a, 10b may be about twice as wide as the strap 14 that is illustrated in FIGS. 1–5. Alternatively, a separate strap 14 may be provided for each of the tourniquet cuffs 10a, 10b. Each such separate strap 14 may be about the same size as the strap 14 of the tourniquet cuff 10 which is illustrated in FIGS. 1–5.

It is understood that the foregoing forms of the invention were described and/or illustrated strictly by way of non-limiting example.

In view of all of the disclosures herein, these and further modifications, adaptations and variations of the present invention will now be apparent to those skilled in the art to which it pertains, within the scope of the following claims.

What is claimed is:

1. A disposable inflatable tourniquet cuff comprising:

a bladder; a stiffener; and a strap;

wherein said bladder comprises fluid-tight inner and outer walls;

wherein said bladder's inner and outer walls each further comprise a pair of respective longitudinal sides having a length, and a pair of respective transverse sides having a width;

wherein said transverse sides are shorter than said longitudinal sides;

wherein longitudinal sides of said bladder's inner wall are sealed to said longitudinal sides of said bladder's outer wall with a pair of longitudinal side welds;

wherein each of said longitudinal side welds has a width;

wherein a ratio of said width of said transverse side to said width of said longitudinal side weld is on the order of from about 18:1 to about 6:1, to enable said pair of longitudinal side welds to stiffen said longitudinal sides to a point that said pair of longitudinal side welds at least partially help to prevent said longitudinal sides of said bladder from curling up towards a longitudinal centerline of said bladder while said bladder is being wound about said patient's limb;

wherein said inner and outer walls each comprise a velcro-type soft, fuzzy surface;

wherein said inner and outer walls form an inflatable space;

wherein said stiffener is located within said inflatable space;

wherein said bladder comprises a fixed end portion and a free portion;

wherein, during use of said tourniquet cuff, said bladder is adapted to be wound about a limb of a patient;

wherein said tourniquet cuff further comprises an anchoring and aligning means;

wherein, as said bladder is wound about said patient's limb, said anchoring and aligning means are for selectively anchoring and aligning said bladder's fixed end portion with respect to an overlapping part of said bladder's free portion, to enable a remaining part of said bladder's free portion to be evenly wound in alignment with, and on top of, a previously wound part of said bladder;

wherein said tourniquet cuff further comprises inflation/deflation means for permitting the entry of a fluid into said inflatable space to inflate said bladder, and for permitting the exit of said fluid out of said inflatable space to deflate said bladder;

wherein, during use of said tourniquet cuff, said strap is adapted to releasably secure said bladder to a limb of a patient;

wherein said strap comprises an anchored portion and a free portion;

wherein said strap's anchored and free portions each comprises velcro-type hooks;

wherein, during use of said tourniquet cuff, at least part of said inner wall's velcro-type soft, fuzzy surface is adapted to be in contact with said patient's limb, and is adapted to provide a comfortable, slip-resistant, contact surface with said patient's limb;

wherein part of said outer wall's velcro-type soft, fuzzy surface is adapted to engage said velcro-type hooks of said strap's anchored portion, to permanently anchor said strap's anchored portion to said outer wall; and wherein, during use of said tourniquet cuff, at least part of said outer wall's velcro-type soft, fuzzy surface is adapted to engage said velcro-type hooks of said strap's free portion, to releasably anchor said strap's free portion to said outer wall.

2. A disposable inflatable tourniquet cuff comprising:

a bladder; and a strap;

wherein said bladder comprises fluid-tight inner and outer walls;

wherein said inner and outer walls each comprise a velcro-type soft, fuzzy surface;

wherein said inner and outer walls form an inflatable space;

wherein said tourniquet cuff further comprises inflation/deflation means for permitting the entry of a fluid into said inflatable space to inflate said bladder, and for permitting the exit of said fluid out of said inflatable space to deflate said bladder;

wherein, during use of said tourniquet cuff, said bladder is adapted to be wound about a limb of a patient;

wherein, during use of said tourniquet cuff, said strap is adapted to releasably secure said bladder to a limb of a patient;

wherein said strap comprises an anchored portion and a free portion;

wherein said strap's anchored and free portions each comprises velcro-type hooks;

wherein, during use of said tourniquet cuff, at least part of said inner wall's velcro-type soft, fuzzy surface is adapted to be in contact with said patient's limb, and is adapted to provide a comfortable, slip-resistant, contact surface with said patient's limb;

wherein part of said outer wall's velcro-type soft, fuzzy surface is adapted to engage said velcro-type hooks of said strap's anchored portion, to permanently anchor said strap's anchored portion to said outer wall; and wherein, during use of said tourniquet cuff, at least part of said outer wall's velcro-type soft, fuzzy surface is adapted to engage said velcro-type hooks of said strap's free portion, to releasably anchor said strap's free portion to said outer wall.

3. The tourniquet cuff according to claim 2, wherein said bladder's inner and outer walls each further comprise a pair of respective longitudinal sides having a length, and a pair of respective transverse sides having a width;

wherein said transverse sides are shorter than said longitudinal sides;

wherein longitudinal sides of said bladder's inner wall are sealed to said longitudinal sides of said bladder's outer wall with a pair of longitudinal side welds;

wherein each of said longitudinal side welds has a width;

wherein a ratio of said width of said transverse side to said width of said longitudinal side weld is on the order of from about 18:1 to about 6:1, to enable said pair of longitudinal side welds to stiffen said longitudinal sides to a point that said pair of longitudinal side welds at least partially help to prevent said longitudinal sides of said bladder from curling up towards a longitudinal centerline of siad bladder while said bladder is being wound about said patient's limb.

4. The tourniquet cuff according to claim 2, wherein said bladder comprises a fixed end portion and a free portion;

wherein said tourniquet cuff further comprises an anchoring and aligning means; and wherein, as said bladder is wound about said patient's limb, said anchoring and aligning means are for selectively anchoring and aligning said bladder's fixed end portion with respect to an overlapping part of said bladder's free portion, to enable a remaining part of said bladder's free portion to be evenly wound in alignment with, and on top of, a previously wound part of said bladder.

5. The tourniquet cuff according to claim 4, wherein said anchoring and aligning means comprises an anchoring and aligning patch;

wherein said patch comprises an inner surface and an outer surface;

wherein said patch's inner surface is secured to said outer wall near said fixed end portion of said bladder;

wherein said patch's outer surface comprises velcro-type hooks; and wherein said patch's velcro-type hooks are adapted to be releasably secured to a corresponding, overlapping part of said inner wall's velcro-type soft, fuzzy surface.

6. The tourniquet cuff according to claim 4, wherein said anchoring and aligning means comprises an anchoring and aligning tab;

wherein said tab comprises an anchored portion and a free portion;

wherein said tab's anchored portion comprises velcro-type hooks;

wherein said tab's free portion comprises velcro-type hooks;

wherein a part of said inner wall's velcro-type soft, fuzzy surface that is located near said bladder's fixed end portion is adapted to engage said velcro-type hooks of said tab's anchored portion, to permanently anchor said tab's anchored portion to said inner wall; and wherein, said velcro-type hooks of said tab's free portion are adapted to be releasably secured to a corresponding, overlapping part of said inner wall's velcro-type soft, fuzzy surface.

7. The tourniquet cuff according to claim 2, wherein said bladder further comprises four corners;

wherein at least one of said corners has a radius, to enable said corner to have an arcuate configuration that is adapted to help to prevent said at least one of said corners from causing discomfort to said patient during use of said tourniquet cuff.

8. The tourniquet cuff according to claim 7, wherein said bladder has a length and a width;

wherein said bladder's length is greater than said bladder's width; and wherein a ratio of said bladder's width to said radius of said at least one corner is on the order of from about 2:1 to about 8:1.

9. A disposable inflatable tournique cuff comprising:

a bladder; and a strap;

wherein said bladder comprises fluid-tight inner and outer walls;

wherein said inner and outer walls form an inflatable space;

wherein said tourniquet cuff further comprises inflation/deflation means for permitting the entry of a fluid into said inflatable space to inflate said bladder, and for permitting the exit of said fluid out of said inflatable space to deflate said bladder;

wherein, during use of said tourniquet cuff, said bladder is adapted to be wound about a limb of a patient;

wherein, during use of said tourniquet cuff, said strap is adapted to releasably secure said bladder to a limb of a patient;

wherein said strap comprises an anchored portion and a free portion;

wherein said strap's anchored portion is permanently anchored to said outer wall with a velcro-type connection; and wherein during use of said tournique cuff, said strap's free portion is adapted to be releasably anchored to said outer wall with a velcro-type connection.

10. The tourniquet cuff according to claim 9, wherein said inner and outer walls each comprises a velcro-type soft, fuzzy sufface;

wherein said strap's anhcored and free portions each comprises velcro-type hooks;

wherien during use of said tourniquet cuff, at least part of said inner wall's velcro-type soft, fuzzy surface is adpated to be in contact with said patient's limb, and is adapted to provide a comfortable, slip-resistant, contact surface with said patient's limb;

wherein part of said outer wall's velcro-type soft, fuzzy surface is adapted to enage said velcro-type hooks of said strap's anchored portion, to permanently anchor said strap's anchored portion to said outer wall; and wherein, during use of said tourniquet cuff, at least part of said outer wall's velcro-type soft, fuzzy surface is adapted to engage said velcro-type hooks of said strap's free portion, to releasably anchor said strap's free portion to said outer wall.

11. The tourniquet cuff according to claim 10 wherein said bladder comprises a fixed end portion and a free portion;

wherein said tourniquet cuff further comprises an anchoring and aligning means; and wherein, as said bladder is wound about said patient's limb, said anchoring and aligning means are for selectively anchoring and aligning said bladder's fixed end portion with respect to an overlapping part of said bladder's free portion, to enable a remaining part of said bladder's free portion to be evenly wound in alignment with, and on top of, a previously wound part of said bladder.

12. The tourniquet cuff according to claim 11, wherein said anchoring and aligning means comprises an anchoring and aligning patch;

wherein said patch comprises an inner surface and an outer surface;

wherein said patch's inner surface is secured to said outer wall near said fixed end portion of said bladder;

wherein said patch's outer surface comprises velcro-type hooks; and wherein said patch's velcro-type hooks are adapted to be releasably secured to a corresponding, overlapping part of said inner wall's velcro-type soft, fuzzy surface.

13. The tourniquet cuff according to claim 12, wherein said anchoring and aligning means comprises an anchoring and aligning tab;

wherein said tab comprises an anchored portion and a free portion;

wherein said tab's anchored portion comprises velcro-type hooks;

wherein said tab's free portion comprises velcro-type hooks;

wherein a part of said inner wall's velcro-type soft, fuzzy surface that is located near said bladder's fixed end portion is adapted to engage said velcro-type hooks of said tab's anchored portion, to permanently anchor said tab's anchored portion to said inner wall; and wherein, said velcro-type hooks of said tab's free portion are adapted to be releasably secured to a corresponding, overlapping part of said inner wall's velcro-type soft, fuzzy surface.

14. The tourniquet cuff according to claim 9, wherein said bladder's inner and outer walls each further comprise a pair of respective longitudinal sides having a length, and a pair of respective transverse sides having a width;

wherein said transverse sides are shorter than said longitudinal sides;

wherein longitudinal sides of said bladder's inner wall are sealed to said longitudinal sides of said bladder's outer wall with a pair of longitudinal side welds;

wherein each of said longitudinal side welds has a width;

wherein a ratio of said width of said transverse side to said width of said longitudinal side weld is on the order of from about 18:1 to about 6:1, to enable said pair of longitudinal side welds to stiffen said longitudinal sides to a point that said pair of longitudianl side welds at least partially help to prevent said longitudinal sides of said bladder from curling up towards a longitudinal centerline of said bladder while said bladder is being wound about said patient's limb.

15. The tourniquet cuff according to claim 9, wherein said bladder further comprises four corners;

wherein at least one of said corners has a radius, to enable said corner to have an arcuate configuration that is adapted to help to prevent said at least one of said corners from causing discomfort to said patient during use of said tourniquet cuff.

16. The tourniquet cuff according to claim 15, wherein said bladder has a length and a width;

wherein said bladder's length is greater than said bladder's width; and wherein a ratio of said bladder's width to said radius of said at least one corner is on the order of from about 2:1 to about 8:1.

* * * * *